(12) United States Patent
Hayashi et al.

(10) Patent No.: US 8,696,983 B2
(45) Date of Patent: Apr. 15, 2014

(54) PLASMA STERILIZING DEVICE AND METHOD

(75) Inventors: Nobuya Hayashi, Saga (JP); Satoshi Kitazaki, Saga (JP)

(73) Assignee: Saga University, Saga-shi, Saga (JP)

( * ) Notice: Subject to any disclaimer, the term of this patent is extended or adjusted under 35 U.S.C. 154(b) by 608 days.

(21) Appl. No.: 12/733,015

(22) PCT Filed: Aug. 4, 2008

(86) PCT No.: PCT/JP2008/063984
§ 371 (c)(1),
(2), (4) Date: Apr. 5, 2010

(87) PCT Pub. No.: WO2009/020105
PCT Pub. Date: Feb. 12, 2009

(65) Prior Publication Data
US 2010/0209292 A1    Aug. 19, 2010

(30) Foreign Application Priority Data

Aug. 3, 2007 (JP) .................................. 2007-203559

(51) Int. Cl.
*A61L 2/00* (2006.01)
*B01J 19/08* (2006.01)
*A01N 1/02* (2006.01)
*A61L 9/00* (2006.01)
*H05H 1/00* (2006.01)

(52) U.S. Cl.
CPC .................. *A01N 1/0294* (2013.01); *A61L 2/00* (2013.01); *A61L 9/00* (2013.01); *H05H 1/0081* (2013.01)
USPC .................... 422/22; 422/1; 422/23; 422/186; 422/186.04; 422/186.05; 422/186.29

(58) Field of Classification Search
CPC .......... A01N 1/0294; A61L 2/00; A61L 9/00; H05H 1/0081
USPC ............... 422/1, 22–23, 186, 186.04–186.05, 422/186.29
See application file for complete search history.

(56) References Cited

U.S. PATENT DOCUMENTS 8,168,130 B2 * 5/2012 Sato et al. ................ 422/186.05
2003/0198570 A1   10/2003 Asahara et al.
(Continued)

FOREIGN PATENT DOCUMENTS

EP         1736175 A1 * 12/2006
EP       1 933 605 A1    6/2008
(Continued)

OTHER PUBLICATIONS

Development of Sterilizing Systems Using Non-Equilibrium Plasma Flow under Atmospheric Pressure, Journal of the Japan Society of Mechanical Engineers, vol. 110, No. 1063, Jun. 2007, p. 56. (English translation of Figure 3).

*Primary Examiner* — Monzer R Chorbaji
(74) *Attorney, Agent, or Firm* — Taft, Stettinius & Hollister LLP

(57) ABSTRACT

A plasma sterilizing device has a container for a long tubule to be sterilized, having an adjustable internal pressure, and an electrode provided at at least one end of the long tubule. The device is configured so that plasma is generated inside the long tubule by applying an alternating current voltage to the electrode in such a state that the pressure inside and outside of the long tubule can be adjusted, so that there is a predetermined difference in pressure between the inside and the outside of the long tubule.

20 Claims, 8 Drawing Sheets

(56) References Cited

U.S. PATENT DOCUMENTS

2005/0019209 A1* 1/2005 Burger et al. .................. 422/23
2008/0193330 A1* 8/2008 Hotta et al. .................... 422/23
2008/0233002 A1* 9/2008 Mizuno et al. ................. 422/22

FOREIGN PATENT DOCUMENTS

| JP | 2002-536071 A | 10/2002 |
| JP | 2003-210556 A | 7/2003 |
| JP | 2003-310719 A | 11/2003 |
| JP | 2006-020950 A | 1/2006 |
| WO | WO 2007/032172 A1 | 3/2007 |
| WO | WO 2007032172 A1 * | 3/2007 |

* cited by examiner

PLASMA STERILIZING DEVICE AND METHOD

TECHNICAL FIELD

This invention relates to a plasma sterilizing device and method, and in particular, to a plasma sterilizing device and method for carrying out a sterilizing process on a long tubule to be sterilized using plasma.

BACKGROUND TECHNOLOGY

Though according to some conventional methods for sterilizing long tubules, such as catheters and endoscopes, ultraviolet rays or high pressure steam is used, the efficiency of sterilization is low, and in some cases the material changes in quality due to the ultraviolet rays or heat. Though other conventional methods using ethylene oxide gas, liquid hydrogen peroxide and steam are highly effective, ethylene oxide and hydrogen peroxide are poisonous, and hydrogen peroxide can be harmful to the handler if it gets on the clothes. In addition, liquids and gases do not reach deep inside the long tubule, due to their viscosity, in accordance with methods other than those using ethylene oxide, and ultraviolet rays are insufficiently transmissive to do so, and thus, it is difficult to sufficiently sterilize long tubules.

Sterilizing methods using plasma have also been proposed, and according to that in Patent Document 1, an electric discharge wire is inserted into the long tubule, so that discharge plasma is generated between the center electrode formed in the discharge wire and an external electrode. According to this method, the discharge wire and an electricity supply wire for supplying power to the discharge wire need to be inserted into the long tubule.

Patent Document 1: Japanese Unexamined Patent Publication 2003-210556

However, it is difficult to make the outer and inner diameter of the discharge wire small in order to avoid conduction between the center electrode and the external electrode and secure a space for discharge between the two, and it is also necessary for the wire to be thick enough, and for insulation between the wires to be secured in order to prevent insulation breakdown in the electricity supply wire. Thus, the long tubules to be sterilized are limited to those having a large inner diameter (for example of 5 mm or more, or 1 cm or more), and in addition, the inner wall of long tubules easily scratches when the discharge wire and electricity supply wire are inserted and removed. Furthermore, when the discharge wire or electricity supply wire makes contact with the inner wall after the sterilization process, bacteria and the like on the surface stick to the inner wall, causing secondary infection. In the case where the same device is used for sterilization, secondary infection becomes a significant problem.

The following Non-Patent Document 1 discloses a sterilizing system for catheters under atmospheric pressure. In this sterilizing system, a wire electrode is inserted into the tubule so that a plasma flow is generated between the wire electrode and a grounding electrode outside the tubule.

Non-Patent Document 1: TOPICS "Development of sterilizing systems using non-equilibrium plasma flow under atmospheric pressure," Journal of Japan Society of Mechanical Engineers, Vol. 110, No. 1063, pp. 56, June 2007.

As in the case of the above described Patent Document 1, however, the insertion of a wire electrode into the tubule risks damaging the inside or causing secondary infection. In addition, there is a risk that the wire electrode may sputter because of the plasma, or that the metal that forms the electrode may make contact with the inside of the tubule along the entire length and causing contamination.

Furthermore, the region where plasma is generated inside the tubule is highly localized between the wire electrode and the grounding electrode. Therefore, a moving mechanism or the like is required in order to move the tubule and the electrodes relative to each other and sterilize the entirety of the inside, making the structure complex and increasing the risk of the inside or outside of the tubule getting damaged, as well as secondary infection. In the case where the grounding electrode is in cylindrical form so that it can surround the tubule, it is necessary to prepare grounding electrodes of different diameters for tubules of different diameters. In addition, there is a risk that the outside of the tubule may be damaged or infected, because the tubule and the grounding electrode are close to each other. Even in the case where the diameter of the grounding electrode is large enough to accommodate for tubules of different diameters, the distance between the wire electrode and the grounding electrode is great, and thus the voltage to be applied to the electrode is high, and as a result, there is a high risk that the wire electrode or the grounding electrode may sputter because of the plasma and contaminate the tubule.

DISCLOSURE OF THE INVENTION

Problem to be Solved by the Invention

The present invention is provided in order to solve the above described problems and provides a plasma sterilizing device and method for generating plasma inside a long tubule to be sterilized, so that a sterilizing process can be carried out inside the long tubule. In particular, the invention provides a plasma sterilizing device and method that can efficiently carry out a sterilizing process in long tubules having an inner diameter of 5 mm or less, prevent damage on the inner or outer wall of the long tubule, reduce the risk of secondary infection, and prevent contamination of the long tubule due to a sputtering electrode.

Means for Solving Problem

The invention according to Claim 1 provides a plasma sterilizing device having: a container for a long tubule to be sterilized having an adjustable internal pressure; and a first electrode provided at least one end of the long tubule, characterized in that plasma is generated inside the long tubule by applying an alternating current to the first electrode in such a state that the pressure inside and outside the long tubule can be adjusted so that there is a predetermined difference in pressure between the inside and the outside of the long tubule.

Here, "sterilizing" in the present invention means not only to kill bacteria but also kill or destroy viruses, and neutralize, decompose or remove proteins and lipids.

The invention according to Claim 2 provides the plasma sterilizing device according to Claim 1, characterized in that a second electrode that faces the first electrode provided at one end is an electrode provided at the other end of the long tubule or a wall of the container.

The invention according to Claim 3 provides the plasma sterilizing device according to Claim 2, characterized in that a through hole for making electrical connection between the inside and the outside of the long tubule is created in one of the electrodes provided at an end of the long tubule.

The invention according to Claim 4 provides the plasma sterilizing device according to Claim 3, characterized in that at least a gas supplying means or a gas discharging means is connected to the through hole so that a gas can enter and leave the long tubule through the through hole.

The invention according to Claim 5 provides the plasma sterilizing device according to any of Claims 1 to 4, characterized in that a means for adjusting the pressure within the container is connected to the container.

The invention according to Claim 6 provides the plasma sterilizing device according to Claim 5, characterized by having a high frequency antenna installed within the container so that plasma can be generated inside the container by applying high frequency voltage to the antenna.

The invention according to Claim 7 provides the plasma sterilizing device according to Claim 6, characterized in that it is possible to apply an alternating current to the first electrode and a high frequency voltage to the antenna at the same time.

The invention according to Claim 8 provides a plasma sterilizing method, characterized in that plasma is generated inside a long tubule to be sterilized through the steps of; providing an electrode at least one end of the long tubule; and applying an alternating current to the electrode in such a state that the pressure inside and outside the long tubule is adjustable so that there is a predetermined difference in pressure between the inside and outside of the long tubule.

The invention according to Claim 9 provides the plasma sterilizing method according to Claim 8, characterized in that plasma is generated by applying a high frequency voltage to the high frequency antenna outside the long tubule at the same time as, or before or after plasma is generated inside the long tubule.

The invention according to Claim 10 provides the plasma sterilizing method according to Claim 8 or 9, characterized in that the pressure inside the long tubule is adjusted so as to be higher or lower than the pressure outside the long tubule before and after plasma is generated inside the long tubule.

The invention according to Claim 11 provides the plasma sterilizing method according to any of Claims 8 to 10, characterized in that the pressure inside the long tubule when plasma is generated is 100 Pa to 10000 Pa and the pressure outside the long tubule is 1/5 or less of the internal pressure.

The invention according to Claim 12 provides the plasma sterilizing method according to Claim 11, characterized in that the alternating current voltage applied to the electrode has a frequency of 1 kHz to 100 kHz and is 1 kV to 10 kV.

The invention according to Claim 13 provides the plasma sterilizing method according to any of Claims 8 to 12, characterized in that the alternating current voltage applied to the electrode has a synthetic waveform gained by synthesizing an alternating current of a predetermined frequency and a pulse having a longer period than this frequency, and the temperature on the surface of the tubule to be sterilized is set to a predetermined temperature or lower during the on period and off period of the pulse.

The invention according to Claim 14 provides the plasma sterilizing method according to any of Claims 8 to 13, characterized in that the long tubule is formed of a resin and has an inner diameter of 5 mm or less and a length of 10 cm or more.

The invention according to Claim 15 provides the plasma sterilizing method according to Claim 14, characterized in that the long tubule is at least partly wound up at the time of the sterilizing process.

The invention according to Claim 16 provides the plasma sterilizing method according to any of Claims 8 to 15, characterized in that a gas containing oxygen or steam is introduced at least into the long tubule.

The invention according to Claim 17 provides the plasma sterilizing method according to any of Claims 8 to 16, characterized in that the long tubule is contained within a resin bag in order to prevent bacteria and viruses from entering.

Effects of the Invention

In accordance with the invention according to Claim 1, an alternating current voltage is applied to an electrode provided at least one end of the long tubule in such a state that the pressure inside or outside the long tubule can be adjusted so that there is a predetermined difference in pressure, and thus, it becomes possible to generate plasma inside the long tubule. As a result, there is glow discharge within the long tubule but no discharge outside the long tubule. Because of the plasma inside the long tubule, it becomes possible to effectively decompose and remove bacteria that cling to the inner wall of the tubule. In particular, the air pressure remains unsuitable for glow discharge outside the long tubule, and therefore there is no discharge, and it becomes possible to generate plasma inside the long tubule by efficiently using the power supplied to the electrode.

When plasma is generated, not only electrons and ions but also ultraviolet rays and radicals are generated. It becomes possible to effectively carry out a sterilizing process using plasma or substances generated as byproducts, so that viruses and bacteria are killed or destroyed and proteins and lipids are neutralized, decomposed and removed. Bacteria are physically destroyed due to ion impulses in the plasma, DNA is destroyed by ultraviolet rays, and the surface of bacteria is etched by radical atoms and molecules, such as oxygen radicals or OH radicals, for example.

Furthermore, In accordance with the present invention, no member is inserted deep into the long tubule, and therefore, a sterilizing process can be carried out even in the case where the inner diameter of the long tubule is 5 mm or less, and in addition, it becomes possible to prevent the inner wall from being damaged, as well as secondary infection. Furthermore, the sputtering electrode does not adhere to the inner wall of the long tubule, and the glow discharge used in the present invention makes it possible to prevent the electrode from sputtering when plasma is generated under atmospheric pressure.

In accordance with the invention according to Claim 2, in the case where the second electrode that faces the first electrode provided at one end is an electrode provided at the other end of the long tubule, the second electrode is easy to attach at the other end of the long tubule in the same manner as the first electrode, and therefore, less work is required than in conventional sterilizing processes, where the electrode is provided within the tubule, and there are no problems with the tubule being damaged. In addition, in the case where the second electrode is a wall of the container, no work is required to attach the second electrode to the long tubule.

In accordance with the invention according to Claim 3, a through hole for making conduction between the inside and outside of the long tubule is created in one of the electrodes provided at an end of the long tubule, and therefore, it is possible to introduce a gas in the long tubule or discharge it, through the through hole. In addition, it is possible to keep a predetermined difference in pressure between the inside and outside of any tubule of any diameter by adjusting the diameter of the through hole, and thus, it is possible to generate plasma efficiently inside the tubule.

In accordance with the invention according to Claim 4, at least a gas supplying means or a gas discharging means is connected to the through hole so that a gas can enter and leave the long tubule through the through hole created in the electrode, and therefore, it is possible to forcibly change the gas within the long tubule. As a result, it becomes possible to introduce a gas that is appropriate for the sterilizing process, such as argon gas, which is easy to convert to plasma or oxygen gas, which is highly effective as a sterilizer into the long tubule, as well as to discharge the gas generated in the sterilizing process from the long tubule.

In accordance with the invention according to Claim 5, the means for adjusting the pressure within the container is connected to the container, and therefore, it becomes possible to adjust the pressure within the container so that the plasma generated by the electrode connected to the long tubule can be prevented from also being generated outside the long tubule and the pressure become suitable for generating the plasma for sterilizing the outer surface of the long tubule within the container, as described below.

In accordance with the invention according to Claim 6, a high frequency antenna is provided within the container so that a high frequency voltage can be applied in order to generate plasma within the container, and therefore, the outer surface of the long tubule can make contact with plasma or oxygen radicals generated by the plasma, so that the surface is sterilized. In particular, the pressure within the long tubule is appropriate for glow discharge, while the inside of the container has lower air pressure, and therefore, it is easy to generate plasma using the high frequency antenna.

In accordance with the invention according to Claim 7, it is possible to apply an alternating current voltage to the electrode and a high frequency voltage to the antenna at the same time, and therefore, it is possible to carry out a sterilizing process on the inner and outer wall of the long tubule at the same time.

In accordance with the invention according to Claim 8, an electrode is provided at least one end of the long tubule to be sterilized and an alternating current voltage is applied to the electrode in such a state that the pressure inside and outside the long tubule can be adjusted so that there is a predetermined difference in pressure between the inside and outside of the long tubule, and therefore, it becomes possible to generate plasma inside the long tubule, as in Claim 1. In particular, there is glow discharge inside the long tubule and no discharge outside the long tubule.

In addition, no member is inserted deep into the long tubule, and therefore, a sterilizing process can be carried out on the long tubule even in the case where the inner diameter is 5 mm or less, and in addition, it is possible to prevent the inner wall from being damaged, as well as secondary infection. Furthermore, the sputtering electrode does not cling to the inner wall of the long tubule, and the glow discharge used in the present invention makes it possible to prevent the electrode from sputtering when plasma is generated under atmospheric pressure.

In accordance with the invention according to Claim 9, plasma is generated outside the long tubule by applying a high frequency voltage to the high frequency at the same time as, or before or after plasma is generated inside the long tubule, and therefore, it is possible to carry out a sterilizing process on the outer wall together with the sterilizing process on the inner wall of the long tubule.

In accordance with the invention according to Claim 10, the pressure inside the long tubule is adjusted to a pressure higher or lower than outside the long tubule before or after plasma is generated inside the long tubule, and therefore, it becomes possible to discharge or intake a gas in the long tubule. As a result, the gas that deteriorates after the sterilizing process within the long tubule is discharged and a fresh external gas (external plasma or radicals in the case where plasma is generated outside) can be taken into the tubule.

In accordance with the invention according to Claim 11, the pressure inside the long tubule when plasma is generated is 100 Pa to 10000 Pa, and the pressure outside the long tubule is ⅕ or less of the internal pressure, and therefore, it is possible to generate plasma through glow discharge inside the long tubule, and at the same time, it is easy to make the environment so that it is difficult to generate outside the long tubule using an alternating power source having a frequency of 1 kHz to 100 kHz and a voltage of 1 kV to 10 kV, for example.

In accordance with the invention according to Claim 12, the alternating current voltage applied to the electrode has a frequency of 1 kHz to 100 kHz and is 1 kV to 10 kV, and therefore, it easy to efficiently generate plasma inside the long tubule by means of glow discharge.

In accordance with the invention according to Claim 13, the alternating current voltage applied to the electrode has a synthetic waveform gained by synthesizing an alternating current having a predetermined frequency and a pulse having a longer period than this frequency, and the temperature on the surface of the tubule to be sterilized is set to a predetermined temperature or lower during the on period and the off period of the pulse, and therefore, it is possible to carry out a sterilizing process using plasma while restricting the increase in the temperature on the surface of the tubule to be sterilized in the case where the heat resistance of the tubule to be sterilized is low, for example when it is made of a resin.

In accordance with the invention according to Claim 14, the long tubule is made of a resin and has an inner diameter of 5 mm or less and a length of 10 cm or more, and therefore, it becomes possible to carry out an appropriate sterilizing process on long tubules for which sufficient sterilization is difficult in accordance with conventional processes when the invention according to Claims 7 to 10 are applied to the long tubule.

In accordance with the invention according to Claim 15, the long tubule is at least partially wound up at the time of the sterilizing process, and therefore, it becomes possible to make the difference in pressure between the inside and outside of the long tubule greater, and thus, it is easy to make the environment so that plasma can be generated only inside the long tubule, for example.

In accordance with the invention according to Claim 16, a gas containing oxygen or steam is introduced at least in the long tubule so that oxygen radicals and OH radicals are generated, and therefore, it is possible to improve the effects of sterilization.

In accordance with the invention according to Claim 17, the long tubule is contained within a resin bag that can prevent bacteria and viruses from entering, and therefore, bacteria and the like can be prevented from clinging to the inside and outside of the long tubule in the packaging process after the sterilization process, and in addition, it also becomes possible to maintain the sterilized state for a long period of time if the long tubule is kept in the resin bag.

| Explanation of Symbols | |
|---|---|
| 1 | long tubule |
| 2 | container |
| 3 | gas discharge valve |
| 4 | gas supply valve |
| 5, 51 to 55, 58 | electrodes |
| 6 | electricity supply wire |
| 7 | alternating current voltage source |
| 8 | base |
| 9, 12 | discharge gas |
| 10, 11 | supply gas |
| 21 | gas supply type |
| 22 | electricity supply terminal |
| 23 | connecting means |
| 24 | tubular electrode |
| 57 | electrode (lead wire) |
| 60 | alternating current voltage |
| 61 | antenna for microwaves |
| 62 | microwaves |

BEST MODE FOR CARRYING OUT THE INVENTION

The plasma sterilizing device and method according to the present invention are described in detail below.
(Structure and Principle of Plasma Sterilizing Device)

Figure 1:
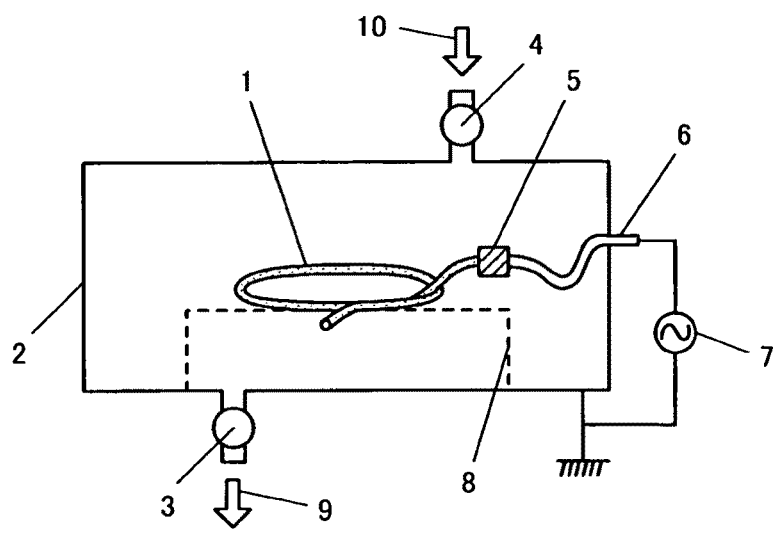
FIG. 1 is a schematic diagram showing the plasma sterilizing device according to the present invention.

FIG. 1 is a schematic diagram showing the plasma sterilizing device according to the present invention.

The plasma sterilizing device according to the present invention is provided with a container 2 for a long tubule 1 to be sterilized having an adjustable internal pressure, and an electrode 5 provided at least one end of the long tubule, and characterized in that plasma can be generated inside the long tubule by applying an alternating current voltage 7 to the electrode in such a state that the pressure inside and outside of the long tubule can be adjusted so that there is a predetermined difference in pressure between the two. Here, the symbol 6 is an electricity supply wire for supplying an alternating current voltage to the electrode 5.

The present invention is characterized in that plasma can be efficiently generated inside the long tubule 1 when there is a predetermined difference in pressure between the inside and the outside of the long tubule 1. The present invention can generally be applied both when the pressure is high inside and outside. In the case where the tubular wall of the long tubule is physically weak, for example, the external pressure, which is higher than the internal pressure, flattens the tubule, thus making it difficult to generate plasma. In addition, it is necessary to connect a pipe for introducing or discharging a gas to the long tubule in order to make the internal pressure lower than the external pressure. In the following description, "long tubule" means a thin, hollow cylinder that is open at the two ends unless otherwise stated.

When the internal pressure of the long tubule is set within a range of 100 Pa to 10000 Pa, it is possible to generate glow discharge, and it is easy to make the environment so that it is difficult to generate plasma outside the long tubule (in particular an environment that does not allow glow discharge to be generated) when the external pressure of the long tubule is $\frac{1}{5}$ or less of the internal pressure, especially when it is $\frac{1}{10}$ or less.

In the case where a long tubule is to be sterilized, in particular a long tubule having an inner diameter of 5 mm or less and a length of 10 cm or more, is used in the plasma sterilizing device according to the present invention, the difference in pressure between inside and outside the long tubule 1 tends to be greater, and therefore, it is easier to set the difference in pressure, as described above.

In addition, the long tubule 1 is at least partially wound up, and thus, it is possible to make the difference in pressure between the inside and the outside of the long tubule greater. In general, when the curvature radius of the wound tubule is smaller, the gas inside the long tubule can be prevented from moving, and thus, it is possible to make the above described difference in pressure greater.

Figure 2:
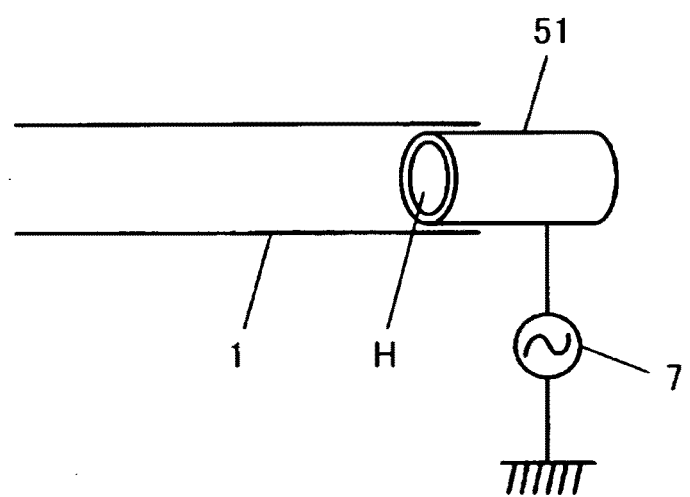
FIG. 2 is a schematic diagram showing an electrode provided at an end of a long tubule.

Furthermore, as shown in FIG. 2, it is possible to create a through hole H to connect the inside and the outside of the long tubule in the electrode 51 that is attached to an end of the long tubule 1. It is also possible to introduce a gas into the long tubule and discharge a gas from the inside through the through hole H. In addition, it is possible to keep a predetermined difference in pressure between the inside and outside of long tubules of different diameters by adjusting the diameter H of the through hole.

In the plasma sterilizing device shown in FIG. 1, a gas supplying means, not shown, a valve 4 for introducing a supply gas 10 into the container through the gas supplying means, a gas discharging means, not shown, and a valve 3 for leading a discharge gas 9 from the container through the gas discharging means are provided in order to adjust the pressure inside the container 2 to a predetermined level.

In addition, it is possible to provide a base 8 on which the long tubule 1 can be placed if necessary. Here, it is preferable for the base 8 to be formed of a non-conductive material, so that there are no problems with generating plasma, as well as to be in net form, so that the base 8 does not prevent the gas from moving within the container.

It is possible to adjust the pressure inside the long tubule to a higher or lower level than outside the long tubule before or after plasma is generated inside the long tubule. As concerns the method for adjusting the pressure, there are methods for periodically changing the pressure within the container 2 at intervals of several minutes, for example, as well as methods for adjusting the internal pressure directly by connecting a gas supplying means or a gas discharging means to the long tubule.

Such adjustment of the pressure makes it possible to discharge a gas that has deteriorated in the sterilizing process inside the long tubule and to intake fresh gas from outside. In addition, in the case where plasma is generated outside the long tubule, external plasma or oxygen radicals can be introduced into the long tubule.

(Tubule to be Sterilized)

The object to be sterilized in the plasma sterilizing device and method according to the present invention is long tubules, concretely, long tubules having an inner diameter of 5 mm or less and a length of 10 cm or more, such as catheters and endoscopes. Though the materials for forming the long tubules are not particularly limited, it is necessary for the tubules them to be formed of a non-conductive material, and the present invention is particularly appropriate for long tubules formed of a resin material, such as silicon rubber, polyimide, vinyl chloride, polyurethane or a fluorine resin.

The present invention makes it possible to sterilize the surface of long tubules, specifically, to get rid of various bacteria clinging to the inner wall, but the present invention is not limited to this, and makes decomposition and removal of lipids and proteins clinging to the inner wall of catheters and the like possible.

(Structure of Electrode)

Figure 3:
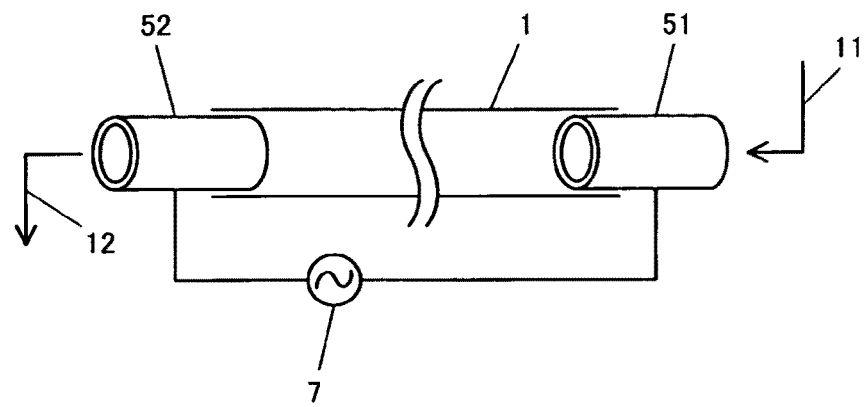
FIG. 3 is a diagram showing two electrodes at either end of a long tubule, each of which having a through hole.

As concerns the electrodes that are attached to the long tubule, as shown in FIG. 2, it is appropriate to insert an electrode 51 into long tubules 1. In addition, it is preferable for a through hole H to be created in the electrode so as to provide a structure where a gas can enter and leave the long tubule 1. FIG. 3 shows an example where electrodes 51 and 52 having a through hole are provided at either end of the long tubule 1. Pipes from a gas supplying means or a gas discharging means are connected to the through holes of the respective electrodes, and thus, as shown in FIG. 3, the structure allows a gas 11 to be forcibly introduced into the long tubule 1 and a gas 12 to be discharged.

At least one of the electrodes for generating plasma inside the long tubule has to be attached to the end of the tubule, but the other electrode may be the main body of the container 2, as shown in FIG. 1, or attached to the other end of the tubule in the same manner as the first electrode, as shown in FIG. 3.

Figure 4A:
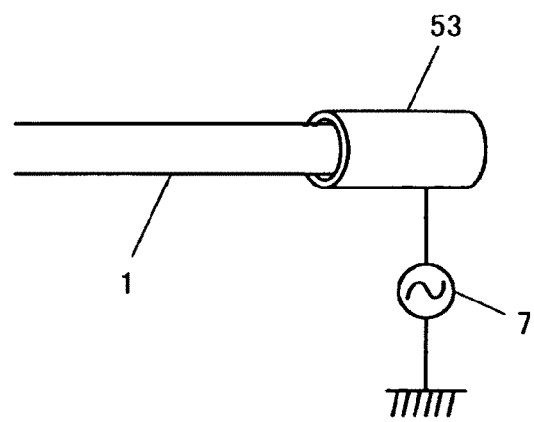
FIG. 4A is a diagram showing an electrode surrounding a long tubule.
Figure 4B:
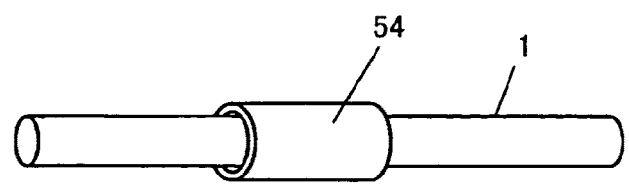
FIG. 4B is a diagram showing an electrode surrounding a long tubule in the middle.

Furthermore, the electrodes need not necessarily be provided inside the tubule as in FIGS. 2 and 3, and as shown in FIG. 4A, it is possible to provide an electrode 53 having an inner diameter that is larger than the outer diameter of the long tubule 1 at the end of the long tubule 1. In addition, as shown in FIG. 4B, it is also possible to provide a tubular electrode 54 in the middle of the long tubule 1 so that plasma can be generated inside the tubule.

Figure 5:
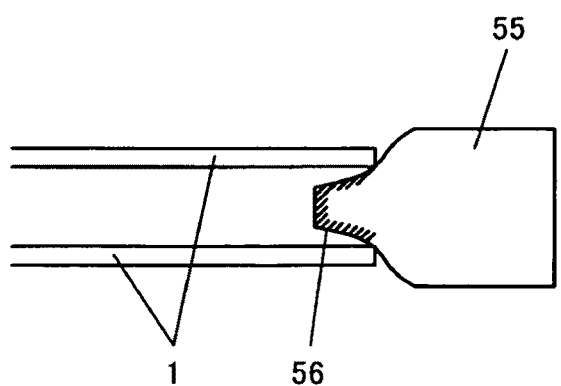
FIG. 5 is a diagram showing another shape for an electrode provided at an end of a long tubule.

As for other forms for the electrode, as shown in FIG. 5, it is possible to form the electrode 55 so that it covers the opening at one end of the long tubule 1.

As concerns the material for forming the electrode, various conductive metals can be used, and metals other than copper, such as gold, aluminum and stainless steel, are appropriate for use for long tubules to be inserted into a human body, for example for medical catheters.

As shown in FIG. 5, the electrode 55 may be formed entirely of such a metal as gold, which is conductive and harmless to the human body, or it is also possible for the surface 56 of the electrode inside the long tubule or the entire surface of the electrode to be plated with gold or the like.

The material for the electrode and the surface process can likewise be used for tubular electrodes, as in FIGS. 2 and 4.

(Driving Method)

The voltage value, frequency and waveform of the alternating current voltage applied to the electrodes attached to the long tubule are set taking into consideration the power required to generate plasma and the ability to carry out a sterilizing process without the long tubule getting damaged by the generated plasma.

The conditions for generating plasma depend on the pressure and material for the gas within the long tubule, and various gases can be used; for example oxygen, mixtures of argon and oxygen, steam or carbon dioxide. In addition, any value within a range of 100 Pa to 10000 Pa can be selected for the pressure within long tubules that make it possible to generate glow discharge using an alternating current voltage.

For the alternating current voltage to be applied, any value within a range of 1 kHz to 100 kHz can be set for the frequency, and any value within a range of 1 kV to 10 kV can be set for the voltage. In the case where the frequency is lower than 1 kHz, it is difficult to sustain glow discharge, and when it exceeds 100 kHz, the temperature inside the long tubule may become too high (for example 70° C. or higher) and the tubule may be damaged. Furthermore, alternating power sources exceeding 100 kHz are expensive and large-scale, and thus may be a problem costwise and spacewise. In addition, a voltage of lower than 1 kV fail to generate glow discharge, while a voltage exceeding 10 kV generates arc discharge and may damage the long tubule in the case where it is formed of a material having low heat resistance, such as a resin.

In addition, in the case where the tubule to be sterilized has low heat resistance, for example in the case where it is formed of a resin, it is necessary to carry out a sterilizing process using plasma while preventing the temperature from increasing on the surface of the tubule to be sterilized. When the voltage value of the alternating current voltage is lower, the energy applied to the plasma lowers, and thus it is possible to prevent the tubule to be sterilized from being damaged, but when the voltage value is too low, it becomes impossible to generate plasma.

Figure 6:
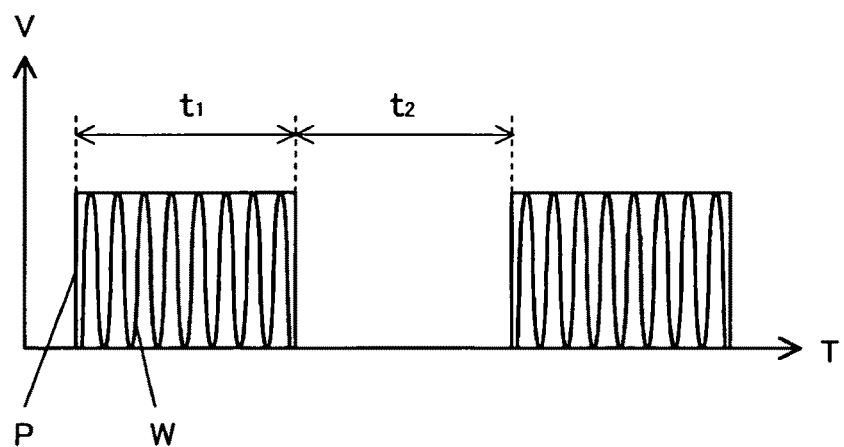
FIG. 6 is a graph showing the waveform of an alternating current voltage applied to an electrode.

Thus, the time for generating plasma is adjusted so as to prevent the temperature on the surface of the tubule to be sterilized from increasing. Concretely, as shown in FIG. 6, the alternating current voltage applied to the electrode has a synthetic waveform gained by synthesizing an alternating current W having a predetermined frequency and a pulse P having a longer period than the frequency, and thus, the on period t1 and the off period t2 of the pulse P are adjusted. 1 pps to 100 pps (pulse per second) is appropriate for the frequency ($1/(t1+t2)$) of the pulse. In addition, the greater the value $t1/(t1+t2)$ is, the higher the temperature of the tubule to be sterilized is, and the greater the value t2 is, the more difficult it is to regenerate plasma. In addition, though in FIG. 6, the maximum value of the pulse P is 1 and the minimum value is 0, it is also possible for the structure to prevent plasma and radical atoms thereof from disappearing completely when the minimum value is set within a range of 0 to 0.5, for example.

(Use of Antibacterial Bag)

In some cases long tubules, such as catheters, are contained in a resin bag up until directly before use in order to prevent bacteria from entering, because it is necessary to prevent bacteria from sticking to the tubule, or prevent the tubule from being otherwise contaminated.

Though the resin bag prevents bacteria from entering, it also has properties that allow gases to enter and leave. A concrete example is bags made of an unwoven sheet gained by combining ultrafine continuous fibers of 100% polyethylene while applying heat and pressure (Tyvek (registered trademark), made by DuPont).

When the task of packaging a long tubule in a resin bag (packaging process) is carried out separately after the sterilizing process on the long tubule, there is a risk that bacteria may cling to the long tubule and enter the resin bag. In order to prevent this problem, as shown in FIG. 7, the present invention allows a sterilizing process to be carried out on the long tubule 1 while inside the resin bag 20.

Figure 7:
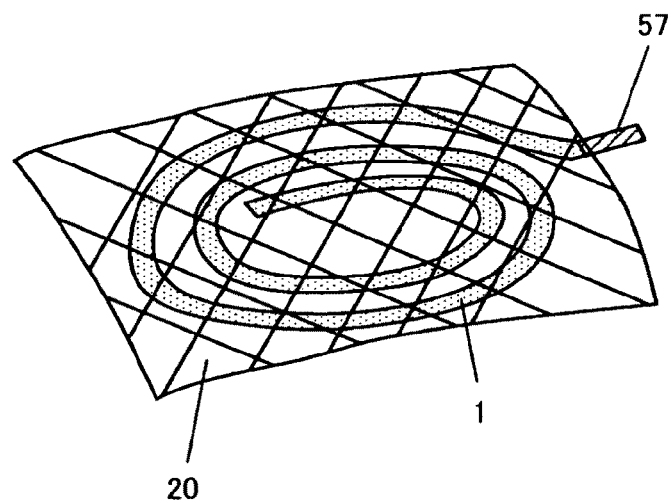
FIG. 7 is a diagram showing a resin bag containing a long tubule.

In order to generate plasma inside the long tubule 1 in such a state that the long tubule 1 is sealed within the resin bag 20, according to the present invention, the lead wire 57 for supplying an alternating current voltage to the electrode provided on the long tubule 1 leads out from the resin bag 20 in a sealed state, as shown in FIG. 7.

In order to sterilize the long tubule contained in the resin bag in FIG. 7, the bag is put in the container 2 and the terminal of the current supply wire 6 in FIG. 1 is connected to the terminal of the lead wire 57 that sticks out from the bag, and thus, plasma can be generated inside the long tubule while maintaining a predetermined pressure inside the container 2, for example. After sterilization is complete, the current supply wire 6 is removed from the lead wire 57 and the long tubule 1 is stored within the resin bag 2, so that the sterilized state can be maintained until the long tubule is used.

(Combination with Sterilizing Device for Outer Surface)

Though the main purpose of the plasma sterilizing device in FIG. 1 is to sterilize the inside of the long tubule 1, it may in some cases also be necessary to sterilize the outer surface of the long tubule. In such cases, it is necessary to generate plasma and oxygen radicals outside the long tubule 1 and inside the container 2. As for the method for generating these, various are applicable, and the method using high frequency (RF) and an antenna described in Patent Document 2 is an appropriate example.

Patent document 2: Japanese Unexamined Patent Publication 2006-20950

Figure 8:
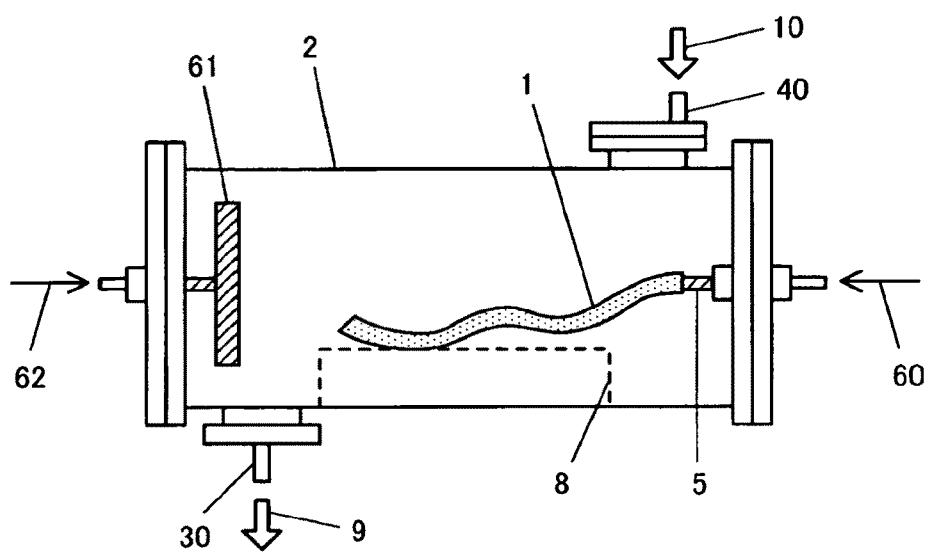
FIG. 8 is a schematic diagram showing a plasma sterilizing device with an antenna for microwaves.

FIG. 8 is a schematic diagram showing a plasma sterilizing device having an extra plasma generator for sterilizing the outside of the long tubule 1. As concerns the method for generating plasma for the outside the long tubule, a high-frequency antenna 61 is provided within the container 2 and a high frequency voltage (RF) 62 of 10 MHz or more is inputted into the antenna.

The pressure outside the long tubule 1 is usually ⅕ or less of the pressure inside the long tubule 1, preferably ¹/₁₀ or less, and therefore, the environment makes it easier for the high frequency voltage to generate plasma. In addition, even when a high frequency voltage 62 (10 MHz or higher) is inputted at the same time as the alternating current voltage 60 (1 kHz to 100 kHz) is applied to the electrode 5 inside the long tubule, the two do not interfere with each other, because their frequencies are two digits or more apart, and thus, it is possible to sterilize the inside and the outside of the long tubule at the same time. It is, naturally, also possible to sterilize the inside and the outside of the long tubule separately.

The symbol 30 in FIG. 8 is a pipe for discharging a gas 9 from the container 2, and the symbol 40 is a pipe for supplying a gas 10 into the container 2.

EMBODIMENTS

Long tubules to be sterilized (made of silicon rubber) having an inner diameter of 2 mm and 4 mm and a length of 50 cm were used, and experiments were carried out in the plasma sterilizing device in FIG. 1.

An electrode 5 was provided only at one end of the long tubule, and the cylindrical container 2 (made of stainless steel and having an inner diameter of 200 mm and a length of 500 mm) was used as a grounding electrode.

An oxygen gas was introduced into the container 2 and the pressure within the container 2 (outside the long tubule 1) was set within a range of 200 Pa to 340 Pa.

Next, an alternating current voltage of 4 kV to 6 kV having a frequency of 10 kHz and a pulse frequency of 10 pps was applied to the electrode 5, as shown in FIG. 6.

Figure 9:
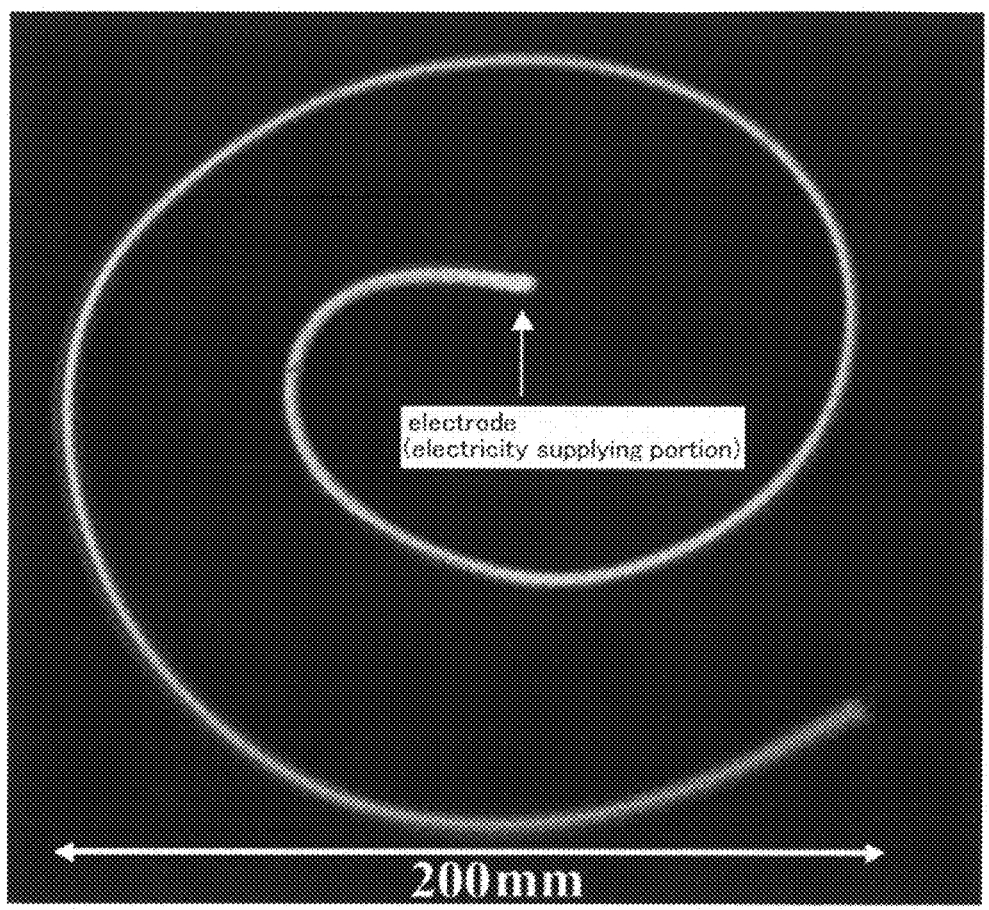
FIG. 9 is a photograph taken in an experiment for generating glow discharge inside a long tubule.

At this time, glow discharge could be confirmed only inside the long tubule. FIG. 9 shows the glow discharge generated inside the long tubule having an inner diameter of 2 mm. It is clear from the figure that plasma was generated stably only inside the long tubule.

Figure 10:
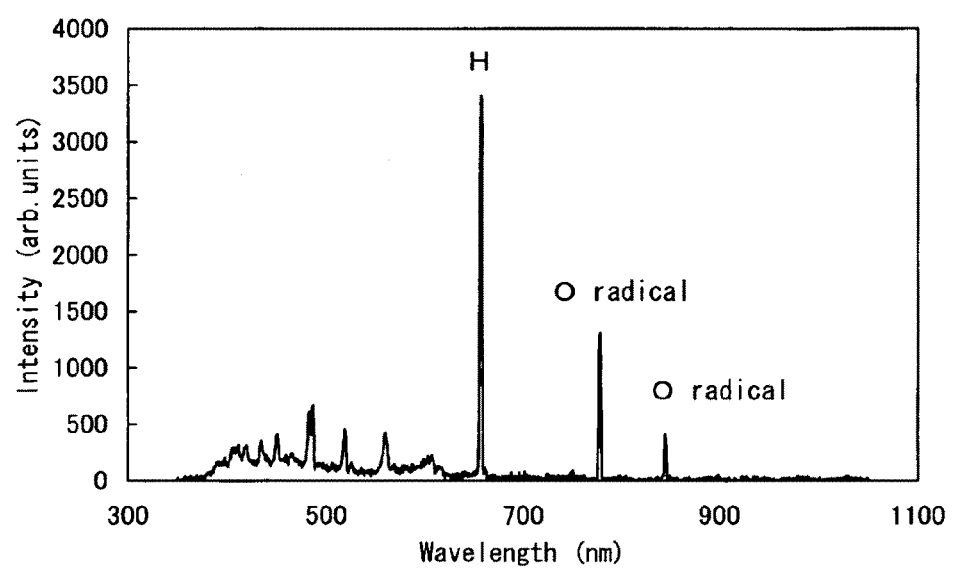
FIG. 10 is a graph showing the spectrogram of the glow discharge in FIG. 9.

In addition, spectral analysis was carried out on light irradiating from the long tubule during glow discharge. Soma Optics S-2400 was used for the spectrometer. FIG. 10 shows the spectrogram. In this spectrogram, the peak for oxygen radicals could be observed at 777 nm. Here, the peak in the spectrum for hydrogen can be assumed to have been generated when moisture clinging to the inside of the long tubule was decomposed by the plasma.

Next, a colony counting test was conducted to confirm the effects of sterilization.

First, test pieces (type of bacteria: *Geobacillus stearothermophilus*, trade name: BACTERIAL SPORE TEST STRIP, manufacturer: Raven Biological Laboratories) were placed 20 cm and 45 cm from the electrode 5 inside the long tubule having an inner diameter of 4 mm.

Next, an oxygen gas was introduced into the container 2, so that glow discharge was generated. Other conditions were the same as in the above.

Discharge was carried out for 6 different times: 1 minute, 3 minutes, 5 minutes, 7 minutes, 10 minutes and 20 minutes, and the test pieces were taken out from the long tubule after the completion of the respective times and cultured on a medium and the colonies were observed. The results are shown in Table 1. Here, cases where a bacterial colony could be observed are indicated by (+) and cases where no colony could be observed after completion of the sterilizing process are indicated by (−).

TABLE 1

| Discharge time | Location of test piece | |
| --- | --- | --- |
| (minutes) | 20 cm | 45 cm |
| 1 | + | + |
| 3 | − | + |
| 5 | − | + |
| 7 | − | + |
| 10 | − | + |
| 20 | − | − |

It is easy to see from Table 1 that it took approximately 3 minutes for the sterilizing process to be completed for 20 cm inside the long tubule, while it took approximately 20 minutes for it to be completed for 45 cm. Accordingly, the plasma sterilizing device and method according to the present invention were effective in sterilizing the tubule and killing bacteria.

Next, a test for the decomposition of protein was conducted in accordance with the following method.

Cow blood, of which the main component is the fibrinogen protein, was applied inside a long tubule (made of silicon rubber) having an inner diameter of 4 mm, and a process was carried out using oxygen plasma, as in the above described method, and the spectrum was taken for the long tubule before and after the process, using an FTIR (infrared ray spectrometer).

In particular, the ratio of decomposition (%) was measured by finding out by how much the peaks corresponding to fibrinogen in the spectrum lowered after the process.

In the case where the plasma process took one hour, a ratio of decomposition of approximately 70% could be achieved, and it could be confirmed that almost complete removal was possible in two hours. It is evident from this that the plasma sterilizing device and method according to the present invention are effective for decomposing protein.

Figure 11A:
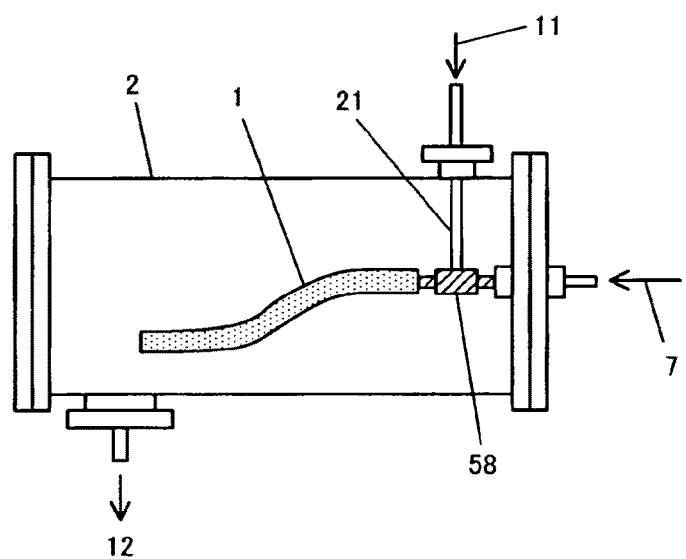
FIG. 11A is a schematic diagram showing a plasma sterilizing device where a gas is introduced into a long tubule from the electrode side.

Next, an experiment was carried out for a long tubule (made of silicon rubber) to be sterilized having an inner diameter of 2 mm and a length of 300 mm in the plasma sterilizing device shown in FIG. 11.

Figure 11B:
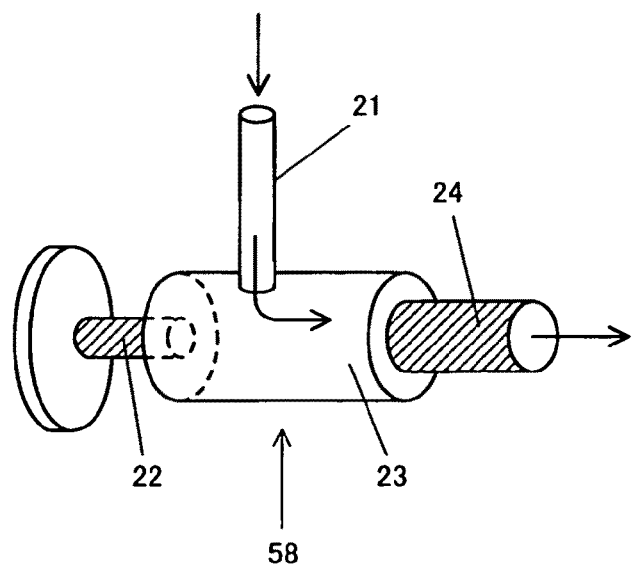
FIG. 11B shows a diagram of the electrode portion of FIG. 11A.

The plasma sterilizing device in FIG. 11 has a structure for introducing a gas into a long tubule 1 from the electrode 58 side. Concretely, as shown in FIG. 11B, a terminal 22 for supplying electricity from the outside is connected to a connecting means 23 made of a metal. The connection means 23 functions to apply an alternating current voltage supplied from the terminal 22 to a tubular electrode 24 to which the long tubule 1 is connected. In addition, a gas supply pipe 21 for supplying a gas made of a non-conductive material (glass or the like) is connected to the connection means 23, and as shown by the arrow in FIG. 11B, the gas within the gas supply pipe 21 is guided to the tubular electrode 24 through the hole in the connection means 23.

The long tubule 1 is connected to the tubular electrode 24 in the electrode 58 and contained in a cylindrical container 2 (made of stainless steel and having an inner diameter of 200 mm and a length of 500 mm), and the container was used as a grounding electrode.

An alternating current voltage 7 and a gas 7 were supplied to the electrode 58 to which the long tubule 1 was connected. In addition, the pressure within the container 2 (outside the long tubule 1) was set to less than 100 Pa within a range of 1 Pa to 30 Pa. The pressure within the container 2 allows the gas supplied from the electrode 58 side to be smoothly discharged through the other end of the long tubule. It is preferable for the pressure to be set so that no plasma is generated outside the long tubule 1 by an alternating current voltage applied to the electrode 58. Therefore, generally, the smaller the inner diameter of the long tubule 1 is and the longer the tubule 1 is, the lower the pressure inside the container 2 should be set.

Though the gas 11 supplied into the long tubule 1 may be only oxygen, a gas supplied through a steam generator was used in the following, and thus, steam and air or steam and oxygen can be used.

An alternating current voltage of 3 kV to 6 kV having a frequency of 10 kHz and a pulse frequency of 10 pps was used, as in FIG. 6.

Figure 12:
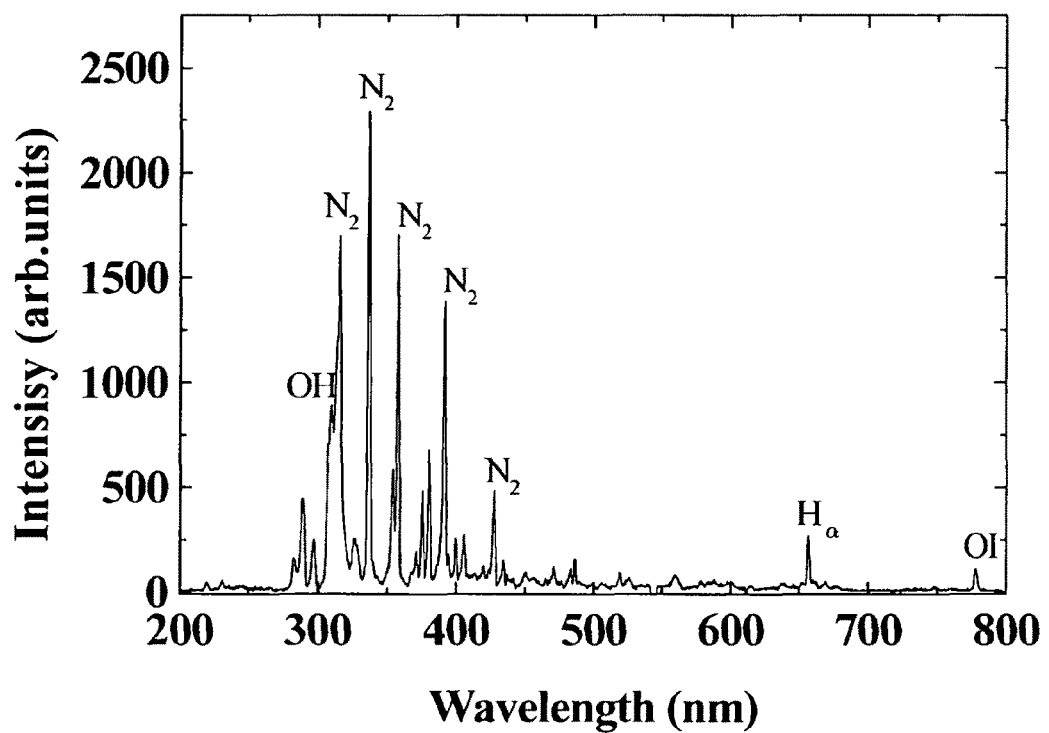
FIG. 12 is a graph showing the spectrogram for discharge when air and steam are introduced into a long tubule.

Air and steam were introduced into the long tubule 1 and glow discharge was generated. At this time, spectral analysis was carried out on the light irradiating from the long tubule. FIG. 12 shows the results. It is easy to see from the results in FIG. 12 that OH radicals were also generated.

Next, a colony counting test was carried out in order to confirm the effects of sterilization.

First, test pieces (type of bacteria: *Geobacillus stearothermophilus*, trade name: BACTERIAL SPORE TEST STRIP, manufacturer: Raven Biological Laboratories) were placed 10 cm, 20 cm and 30 cm from the electrode 5 inside the long tubule having an inner diameter of 4 mm.

Next, oxygen gas and steam were introduced into the long tubule and glow discharge was generated. Other conditions were the same as in the above.

Discharge was carried out for 3 different times: 1 minute, 5 minutes and 10 minutes, and the test pieces were taken out from the long tubule after the completion of the respective times and cultured on a medium and the colonies were observed. The results are shown in Table 2. Here, cases where a bacterial colony could be observed are indicated by (+) and cases where no colony could be observed after completion of the sterilizing process are indicated by (−).

TABLE 2

| Discharge time | Location of test piece | | |
|---|---|---|---|
| (minutes) | 10 cm | 20 cm | 30 cm |
| 1 | − | − | + |
| 5 | − | − | − |
| 10 | − | − | − |

It is easy to see from Table 2 that it took approximately 1 minute for the sterilizing process to be completed for 20 cm inside the long tubule having an inner diameter of 2 mm, while it took approximately 5 minutes for it to be completed for 30 cm. Accordingly, the plasma sterilizing device and method according to the present invention were effective in sterilizing the tubule and killing bacteria.

INDUSTRIAL APPLICABILITY

As described above, the present invention can provide a plasma sterilizing device and method for generating plasma within a long tubule to be sterilized, so that a sterilizing process can be carried out inside the long tubule. In particular, the invention can provide a plasma sterilizing device and method according to which an efficient sterilizing process can be carried out on a long tubule having an inner diameter of 5 mm or less, and at the same time, it is possible to prevent the inner wall of the long tubule from being damaged and reduce the risk of secondary infection, and it is possible to prevent the long tubule from being contaminated by a sputtering electrode.

The invention claimed is:

1. A plasma sterilizing device, comprising:
    a container having means adapted to adjust a gas pressure inside the container, the inside dimensions of the container being such that it can accommodate a long tubule to be sterilized;
    a first electrode positioned and adapted to be attached to a first end of the long tubule when the long tubule is placed within the container; and
    a second electrode, wherein
    pressure adjusting means are provided for adjusting a gas pressure inside the long tubule, when the long tubule is placed with the container, so that plasma can be generated inside the long tubule, when the long tubule is placed within the container, by applying an alternating current to the first electrode in a state that the pressure inside the long tubule when plasma is generated is 100 Pa to 10000 Pa and the pressure outside the long tubule is ⅕ or less of the pressure inside the long tubule.

2. The plasma sterilizing device according to claim 1, wherein the second electrode faces the first electrode when the long tubule is placed within the container, and the second electrode is positioned at an opposite end of the long tubule when the long tubule is placed within the container.

3. The plasma sterilizing device according to claim 2, wherein a through hole for making electrical connection between the inside and the outside of the long tubule is formed in one of said first and second electrodes when the long tubule is placed within the container.

4. The plasma sterilizing device according to claim 3, wherein at least a gas supplying means or a gas discharging means is connected to the through hole for passage of a gas into and out of the long tubule through the through hole when the long tubule is placed within the container.

5. The plasma sterilizing device according to claim 1, further comprising a high frequency antenna installed within the container, said antenna being adapted so that plasma is generated inside the container by application of high frequency voltage to the antenna.

6. The plasma sterilizing device according to claim 5, further comprising a first electrical supply connection adapted to apply an alternating current to the first electrode, and a second electrical supply connection adapted to apply a high frequency voltage to the antenna at the same time.

7. A plasma sterilizing method, comprising the step of generating plasma inside a long tubule to be sterilized, said generating step comprising the steps of:
attaching an electrode to a first end of the long tubule; and
applying an alternating current to the electrode in a state wherein pressure inside and outside the long tubule is adjustable so that the pressure inside the long tubule when plasma is generated is 100 Pa to 10000 Pa and the pressure outside the long tubule is ⅕ or less of the pressure inside the long tubule.

8. The plasma sterilizing method according to claim 7, wherein a high frequency antenna is provided outside the long tubule and plasma is generated by applying a high frequency voltage to a high frequency antenna outside the long tubule at a same time as, or before or after plasma is generated inside the long tubule.

9. The plasma sterilizing method according to claim 8, wherein the pressure inside the long tubule is adjusted to be higher or lower than the pressure outside the long tubule before and after plasma is generated inside the long tubule.

10. The plasma sterilizing method according to claim 8, wherein alternating current voltage applied to the electrode has a synthetic waveform gained by synthesizing an alternating current of a predetermined frequency and a pulse having a longer period than said frequency, and a temperature on a surface of the tubule to be sterilized is set to a predetermined temperature or lower during an on period and an off period of the pulse.

11. The plasma sterilizing method according to claim 7 wherein the pressure inside the long tubule is adjusted to be higher or lower than the pressure outside the long tubule before and after plasma is generated inside the long tubule.

12. The plasma sterilizing method according to claim 11, wherein alternating current voltage applied to the electrode has a synthetic waveform gained by synthesizing an alternating current of a predetermined frequency and a pulse having a longer period than said frequency, and a temperature on a surface of the tubule to be sterilized is set to a predetermined temperature or lower during an on period and an off period of the pulse.

13. The plasma sterilizing method according to claim 7, wherein alternating current voltage applied to the electrode has a frequency of 1 kHz to 100 kHz, and is 1 kV to 10 kV.

14. The plasma sterilizing method according to claim 7, wherein alternating current voltage applied to the electrode has a synthetic waveform gained by synthesizing an alternating current of a predetermined frequency and a pulse having a longer period than said frequency, and a temperature on a surface of the tubule to be sterilized is set to a predetermined temperature or lower during an on period and an off period of the pulse.

15. The plasma sterilizing method according to claim 7, wherein the long tubule is formed of a resin and has an inner diameter of 5 mm or less and a length of 10 cm or more.

16. The plasma sterilizing method according to claim 15, wherein the long tubule is at least partly wound up at a time of the sterilizing process.

17. The plasma sterilizing method according to claim 7, wherein a gas containing oxygen or steam is introduced at least into the long tubule.

18. The plasma sterilizing method according to claim 7, wherein the long tubule is contained within a resin bag to prevent entry of bacteria and viruses.

19. A plasma sterilizing device, comprising:
a container having means adapted to adjust a gas pressure inside the container, the inside dimensions of the container being such that it can accommodate a long tubule to be sterilized;
a first electrode having an inner diameter that is larger than an outer diameter of the long tubule and adapted to be positioned at a first end of the long tubule when the long tubule is placed within the container; and a second electrode, wherein
pressure adjusting means are provided for adjusting a gas pressure inside the long tubule, when the long tubule is placed with the container, so that plasma can be generated inside the long tubule, when the long tubule is placed within the container, by applying an alternating current to the first electrode in a state that the pressure inside the long tubule when plasma is generated is 100 Pa to 10000 Pa and the pressure outside the long tubule is ⅕ or less of the pressure inside the long tubule.

20. A plasma sterilizing device, comprising:
a container having means adapted to adjust a gas pressure inside the container, the inside dimensions of the container being such that it can accommodate a long tubule to be sterilized;
a first electrode having an inner diameter that is larger than an outer diameter of the long tubule and adapted to be positioned in the middle of the long tubule when the long tubule is placed within the container; and a second electrode, wherein
pressure adjusting means are provided for adjusting a gas pressure inside the long tubule, when the long tubule is placed with the container, so that plasma can be generated inside the long tubule, when the long tubule is placed within the container, by applying an alternating current to the first electrode in a state that the pressure inside the long tubule when plasma is generated is 100 Pa to 10000 Pa and the pressure outside the long tubule is ⅕ or less of the pressure inside the long tubule.

* * * * *